United States Patent
Raymond et al.

(10) Patent No.: US 7,372,942 B2
(45) Date of Patent: May 13, 2008

(54) MEDICAL IMAGING SYSTEM WITH DOSIMETRY FOR ESTIMATING CIRCUIT BOARD LIFE

(75) Inventors: Douglas William Raymond, Orinda, CA (US); Carlos E. Medina, Concord, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 46 days.

(21) Appl. No.: 11/092,014

(22) Filed: Mar. 28, 2005

(65) Prior Publication Data

US 2005/0213706 A1 Sep. 29, 2005

Related U.S. Application Data

(60) Provisional application No. 60/557,524, filed on Mar. 29, 2004.

(51) Int. Cl.
- H05G 1/42 (2006.01)
- H05G 1/44 (2006.01)
- G01T 1/02 (2006.01)
- G01T 1/142 (2006.01)

(52) U.S. Cl. .................... 378/97; 250/370.07

(58) Field of Classification Search ............. 250/484.5, 250/370.01, 370.07–8, 370.08; 378/97, 108, 378/207, 65
See application file for complete search history.

(56) References Cited

U.S. PATENT DOCUMENTS

| | | | |
|---|---|---|---|
| 4,027,164 A * | 5/1977 | Larsen et al. ............. 250/372 |
| 4,415,237 A | 11/1983 | Fox | |
| 4,484,076 A | 11/1984 | Thomson | |
| 4,774,643 A | 9/1988 | McGinnis et al. | |
| 4,816,753 A * | 3/1989 | Palkuti ....................... 324/501 |
| 4,839,518 A | 6/1989 | Braunlich et al. | |
| 5,079,426 A * | 1/1992 | Antonuk et al. ........ 250/370.09 |
| 5,084,873 A * | 1/1992 | Houston ........................ 714/48 |
| 5,317,252 A * | 5/1994 | Kranbuehl ................... 324/71.1 |
| 5,430,308 A * | 7/1995 | Feichtner et al. ............ 250/580 |
| 5,585,638 A * | 12/1996 | Hoffman ................. 250/370.07 |
| 5,596,199 A | 1/1997 | McNulty | |
| 5,672,918 A * | 9/1997 | Kimbrough et al. ......... 307/126 |
| 5,753,920 A * | 5/1998 | Buehler et al. ........ 250/370.06 |
| 5,905,262 A | 5/1999 | Spanswick | |
| 5,949,811 A * | 9/1999 | Baba et al. ................. 378/108 |
| 5,966,425 A * | 10/1999 | Beland ....................... 378/108 |
| 6,067,343 A * | 5/2000 | Brendler et al. ............ 378/98.7 |
| 6,141,402 A * | 10/2000 | Toth ........................... 378/150 |
| 6,192,105 B1 * | 2/2001 | Hunter et al. ............... 378/108 |
| 6,275,747 B1 * | 8/2001 | Wada et al. ................. 700/266 |

(Continued)

OTHER PUBLICATIONS

Zontar, D., Radiation Monitoring at Belle, Mar. 2003, Elsevier, vol. 501 (1), pp. 164-166.*

(Continued)

Primary Examiner—Edward J. Glick
Assistant Examiner—Anastasia S. Midkiff

(57) ABSTRACT

A dosimeter is provided on or adjacent to a circuit board deployed in a radiation environment. The dosimeter may be read or output a value or values indicating radiation dosage over a period of time. The radiation dosage associated with the circuit board may be used for determining disposition of the circuit board, such as whether to reuse the circuit board as a spare part or otherwise dispose of the circuit board.

20 Claims, 1 Drawing Sheet

U.S. PATENT DOCUMENTS

| | | | |
|---|---|---|---|
| 6,404,851 B1 * | 6/2002 | Possin et al. | 378/98.7 |
| 6,717,154 B2 | 4/2004 | Black et al. | |
| 2002/0085673 A1 * | 7/2002 | Rinaldi et al. | 378/108 |
| 2003/0133534 A1 * | 7/2003 | Bothe et al. | 378/16 |
| 2004/0065839 A1 * | 4/2004 | Elgali | 250/370.11 |

OTHER PUBLICATIONS

"Microsensors—Ionizing Radiation Sensor RADFET Dosimeter Provides Reliable Ionizing Radiation Measu," http://www.mdl.sandia.gov/mstc/technologies/microsensors/radiationsensor.html; printed on Feb. 24, 2005; 3 pages.

"The RADFET," RADFET Technical Information at Tyndall National Institute; http://www.tyndall.ie/projects/radfets/tech.html; Printed on Feb. 24, 2005; 6 pages.

FDC5614P—60V P-Channel Logic Level Power Trench® MOSFET; dated Feb. 2002; Fairchild Semiconductor™ Corporation; 5 pages.

BSS84—P-Channel Enhancement Mode Field Effect Transistor; dated Jul. 2002; Fairchild Semiconductor™ Corporation; 5 pages.

* cited by examiner

MEDICAL IMAGING SYSTEM WITH DOSIMETRY FOR ESTIMATING CIRCUIT BOARD LIFE

RELATED APPLICATIONS

The present patent document claims the benefit of the filing date under 35 U.S.C. §119(e) of Provisional U.S. Patent Application Ser. No. 60/557,524, filed Mar. 29, 2004, which is hereby incorporated herein by reference.

BACKGROUND

The present invention relates to determining radiation dosage. In particular, radiation dosage associated with medical therapy or imaging is determined.

Medical imaging or therapy systems may generate radiation. For example, x-ray systems, computed tomography systems or x-ray therapeutic systems generate radiation. A linear accelerator generates x-ray photons. The dosage of x-ray photons supplied to a patient is regulated or limited. A detector is positioned to determine a dosage of x-ray photons applied to the patient. For example, a detector is positioned between the linear accelerator and a patient area for determining the dose of radiation output by the linear accelerator.

Radiation may impact on other components within the systems, such as circuit boards. The linear accelerator control system connects with the dose detector. The circuit board for the control system may be within a radiation environment. Most of the radiation produced by the accelerator is directed at the patient, but a certain amount of radiation is emitted in random directions, and it is not practical to shield all the radiation. The extra radiation, if it impinges on circuits and circuit boards, may cause the circuits or circuit boards to deteriorate over the life of the medical system.

Individual circuit boards may be replaced at various times for various reasons. Typically, the reasons are unrelated to radiation exposure. A service engineer removes the board and returns the board to a manufacturer. The returned boards are evaluated, possibly repaired, and then returned to the stock of replacement parts. However, it is difficult to predict when a subsequent failure may occur. The uncertainly is expensive. If all returned boards were discarded, then valuable boards with substantial life may be unnecessarily discarded. If all working circuit boards were returned, then service problems may be generated by circuit boards with minimal remaining useful life.

BRIEF SUMMARY

By way of introduction, the preferred embodiments described below include methods and systems for estimating circuit life. A dosimeter is provided on or adjacent to a circuit board deployed in a radiation environment. The dosimeter may be read or output a value or values indicating radiation dosage that is accumulated over a period of time. The circuit board radiation dosage may be used for determining disposition of the circuit board, such as whether to reuse the circuit board as a spare part or otherwise dispose of the circuit board.

In a first aspect, a system is provided for estimating circuit life. A medical imaging or treatment systems includes a circuit. A dosimeter is adjacent to the circuit. The dosimeter is responsive to radiation exposure of the circuit based on its position adjacent to the circuit.

In a second aspect, a method is provided for estimating circuit life in a radiation based medical system. Radiation is generated with the medical system. Radiation exposure of a circuit is measured. A remaining life of the circuit is estimated as a function of the measured radiation exposure.

In a third aspect, a system is provided for estimating circuit life due to exposure to medical treatment or imaging radiation. A radiation source is oriented relative to a patient area. A dosimeter connects with a circuit board of the system.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

One or more circuit boards used in a radiation environment of a medical system include a dosimeter. The dosimeter records the amount of radiation received by the circuit board or circuit. A decision criterion, or set of decision criteria based on accelerated life testing is used in conjunction with the knowledge of the current state of the dosimeter to decide whether it is more economical to scrap a used board or recondition the used board for additional service. Dosimeter monitoring as part of the normal function of the circuit board provides an indication of the health of the board in the medical system. A dosimeter whose accumulated dose value can be read out non-destructively—that is, one that can be read without disturbing the stored value—is generally more trustworthy, because the current value depends only on the radiation the board has been cumulatively exposed to, and does not depend on how many times the board has been previously read out. An early warning signal may also be provided from the dosimeter to a display associated with the medical system. Without such a dosimeter, the radiation history of the board would be unknown. Radiation uncertainty regarding the life of a circuit board is limited or removed by keeping a record of radiation exposure for a circuit.

Figure 1:
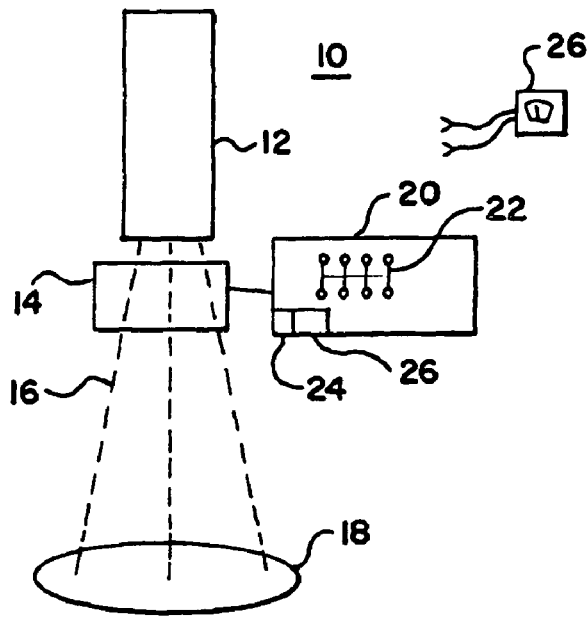
FIG. 1 is a block diagram showing one embodiment of a medical system with a dosimeter for circuit board life estimation.

FIG. 1 shows one embodiment of a system 10 for estimating circuit life. Circuit life due to exposure to medical treatment or imaging radiation is estimated. The system 10 includes an x-ray source 12, a dosage detector 14, a beam value 16, a patient area 18, a circuit board 20, a circuit 22, a dosimeter 24 and a measurement circuit 26. Additional, different or fewer components may be provided. For example, the medical system 10 is provided without the dosage detector 14 and/or one of the two measurement circuits 26. The system 10 is a medical imaging or treatment system. For example, the system 10 is an x-ray therapy system, an x-ray imaging system, a computed tomography system, or other medical system that generates radiation during at least a portion of the operation of the system.

The radiation source 12 is a linear accelerator. Other sources of radiation may be used. The radiation source 12 generates a beam 16 of radiation directed towards the patient area 18. The beam 16 and the direction may be determined by the radiation source 12, collimators or combinations of both. Radiation in addition to the beam may be generated in other areas around or adjacent to the radiation source 12. During operation of the medical system 10, the radiation source 12 generates one or more pulses of radiation for imaging or treating a patient in the patient area 18 with the radiation beam 16.

The circuit 22 includes a plurality of electrical components on the circuit board 20. The circuit 22 may be distributed over multiple circuit boards 20 or free of any circuit board 20. The circuit 22 is used within the medical system 10 for data processing, monitoring, image processing, display, configuration, operation control or other purpose. In the embodiment shown in FIG. 1, the circuit 22 connects with the dosage detector 14. The circuit 22 operates as a linear accelerator control system to read the dosage generated by the radiation source 12. A plurality of amplifiers, filters, integrators, digital multipliers, analog multipliers, comparators, control devices or other digital or analog circuits are provided in one or multiple redundant paths. In response to a patient dosage generated or detected by the detector 14, the circuit 22 monitors a total exposure of a patient during a given session and/or limits the generation of radiation by the radiation source 12.

The circuit 22 is spaced away from the beam 16. For example, the circuit 22 and associated circuit board 20 connect with the dosage detector 14 adjacent to the radiation source 12. The circuit board 20 and circuit 22 are positioned spaced away from the beam volume 16, such as being about a foot away from a possible outer edge of the beam volume 16. Alternatively, the circuit 22 is positioned where at least a portion of the circuit 22 or associated circuit board 20 is within a possible beam volume 16.

Different components of the circuit 22 may absorb different amounts of radiation over the life of the component and continue to work acceptably. By testing various components, some may be found more susceptible to radiation damage, such as power amplifiers or switching regulators. Alternatively, dosage limits are identified for an entire circuit 22 or circuit board 20 without determination associated with specific components. Rather than determining dosage susceptibility, an estimation or predicted susceptibility may be provided. In general, components are selected to better withstand radiation. Components of the circuit 22 in hotter spots on a circuit board 20 may be subjected to larger amounts of radiation. In one example case, a board receives an exposure over a ten year design life that is the equivalent of 520,000 isocenter MU One isocenter MU is equal to the ionizing energy of one centigray in water at isocenter. Greater or lesser amounts of radiation may be incident on a given circuit 22 over a same or different time period. For example, one medical system 10 may be used more frequently than another medical system 10. As another example, the course of therapy or variation in radiation dosage applied to the patient may be different at different times or for different facilities.

The dosimeter 24 is a RADFET, commercial off the shelf transistor, copy or same component as a weakest or other component within the circuit 22, combinations thereof or other now known or later developed device responsive to dose over a desired range of time or radiation exposure. The dosimeter 24 is operable to output the stored radiation exposure value without disturbing that stored value, allowing continued use and accumulation of dose to accurately represent the dosage received by the circuit 22 and circuit board 20 through multiple tests or measurements throughout the service life. The dosimeter 24 is operable over a range of radiation exposure corresponding to the expected exposure to the time of expected failure of a weakest component of the circuit 22 or other range. The dosimeter 24 is operable to indicate an amount of dosage until the expected failure of the circuit 22. Alternatively, the dosimeter is operable to detect a range of exposure less than the expected life due to radiation exposure of a weakest component on the circuit 22. For example, the circuit 22 is not likely to be repaired and returned to service, where only a year or two remain in the life of the circuit based on the circuit's record of radiation exposure. As long as the dosimeter 24 is operable over a range of dosage up until the cutoff point for discarding the circuit 22, the dosimeter 24 may provide a useful indication of expected life of the circuit 22.

The dosimeter 24 is small, such as a RADFET or transistor, so as not to limit circuit board space. In one embodiment, the dosimeter 24 consumes minimal amounts of power and retains its state or dosage reading even when power is removed and reapplied repeatedly. By being of a non-destructive readout variety, the dosimeter 24 may be read without having its state disturbed. The dosimeter 24 may be resetable or non-resetable. The dosimeter 24 is responsive to the type of radiation generated by the radiation source or multiple different types of radiation where different components of the circuit 22 degrade differently in response to different types of radiation.

Figure 2:
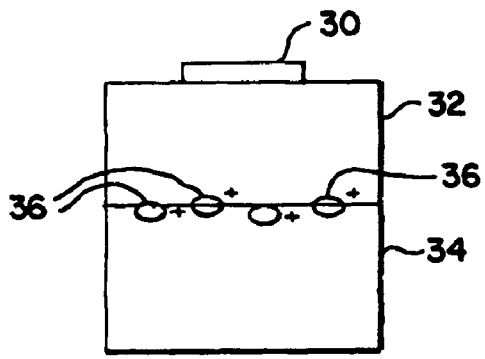
FIG. 2 is a graphical representation of the possible effect of incident radiation on a transistor in one example.

Components that are damaged by radiation may be used as the dosimeter 24. For example, radiation damages MOSFET transistors. FIG. 2 shows one exemplarily MOSFET transistor. The transistor includes a metal field effect transistor gate 30, a passivating oxide layer 32 and a crystalline silicon layer 34. Due to exposure to X-rays, positive charges 36 gradually accumulate in the gate oxide layer 32 or at the boundary of the gate oxide layer 32 with the silicon layer 34. As a photon passes through the gate oxide or other portion of the transistor, an electron hole pair is generated. If the pair does not immediately recombine, the more mobile electron may move into the conductive gate material or body of the transistor. The positive hole may often be trapped in a natural dislocation in the crystalline lattice in the oxide silicon boundary. The trapped positive holes create a positive electric field that is equivalent to having applied a positive voltage at the gate. To return the transistor to its original pre-exposure operating point, it's necessary to bias the gate to a more negative potential. As exposure increases, the necessary additional negative potential increases. The mechanism that traps the holes at the oxide/silicon boundary is a robust one. The trapped holes cannot be removed by normal externally applied stimuli at ordinary temperatures, so the readout is non-destructive.

Either of a p-channel or n-channel device may be used as the dosimeter 24. In a p-channel MOSFET, the trapped charge may be more easily measured than an n-channel. For p-channel device, the gate terminal is driven more negative to cancel out the field generated by accumulated positive charges. The threshold voltage starts out negative and becomes more negative with increasing cumulative radiation exposure. The threshold voltage is measured to indicate a radiation dosage. The threshold voltage in an N-channel MOSFET may eventually reach zero, rendering the transistor threshold no longer measurable. In a P-channel MOSFET, the threshold voltage is already negative, and can continue to grow more negative for several volts, providing a greater range than for an N-channel MOSFET. Since the trapped charge is trapped permanently, the dosimeter 24 is read out non-destructively. The shift in the threshold over time and exposure represents a total effect from all the radiation exposure ever delivered to the dosimeter 24.

The electron half of the electron hole pair is more likely to be swept out of the oxide 32, leaving a positively charged hole behind, where an electric field exists across the gate oxide 32. To increase sensitivity, the dosimeter 24 may be kept powered on during possible exposure to radiation. A more sensitive measurement may be provided by biasing the dosimeter 24 whenever potential radiation exposure exists, such as during the operation of the system 10 or the radiation source 12. Alternatively, the dosimeter 24 is unpowered during exposure to radiation.

The dosimeter sensitivity may depend on the thickness of the gate oxide 32. Since photons typically interact with the oxide 32, a thinner oxide layer may generate fewer electron hole pairs. A shorter distance is provided to escape the bulk silicon 34. Accordingly, a thinner oxide 32 is less sensitive to radiation exposure. In alternative embodiments, other effects or causes of change due to radiation exposure may be used for the dosimeter 14.

A RADFET is a p-channel MOSFET. The RADFET is designed for sensing radiation dosage. Rather than sensing human tolerable amounts of radiation, the RADFET used herein may be exposed to a greater amount of radiation over a longer amount of time, such as operable to record the equivalent of a million MU at isocenter.

As an alternative to a RADFET, a commercial off-the-shelf transistor is used for the dosimeter 24. Commercial off-the-shelf transistors are manufactured in high volume and sold for use in different applications. Parts are generally available and typically have a constant design over the many years that they remain in production. For example, p-channel transistors manufactured by Fairchild under product names BSS84 and FDC5614P are used. Other transistors by other manufacturers with the same, similar or different characteristics may be used. Since the dosimeter 24 is not used to regulate patient dosage, a device subject to regulatory approval may not be necessary. Other devices having desired linear, non-linear, experimentally determined or known characteristics as a function of dosage may be used.

A commercial off-the-shelf transistor is calibrated for use as the dosimeter 24. The threshold voltage of several or many new samples of the transistor is measured. The transistors are exposed to a known amount of radiation. The threshold voltages of the transistors are remeasured. The exposure and remeasurements may be repeated until the threshold voltage can no longer be measured or another criterion (e.g., total amount of exposure) is met. Graphs of the thresholds verses accumulated exposure and statistical distribution are then used to determine a likely or average relationship of exposure to threshold voltage.

Where one or more components of the circuit 22 are identified as most likely weakest or most sensitive to radiation, a similar or same part may be used as the dosimeter 24. Any measurable characteristic whose changes can be quantitatively calibrated against accumulated radiation exposure, such as current, voltage, power, resistance, capacitance, impedance or other now known or later developed circuit component characteristic may be measured to indicate dosage. For example, the offset voltage in an operational amplifier may change monotonically as a function of dose. By using the operational amplifier in a high gain state with the positive input grounded, the offset voltage is measured. The offset voltage may provide an indication of the total amount of accumulated radiation received by the amplifier since manufacture. Where a plurality of amplifiers is used in the circuit 22, one or more amplifiers may be provided on a same integrated circuit for minimal cost to be used as dosimeters. This choice is useful when said amplifiers respond to accumulated radiation dosage in ways that can be calibrated. Alternatively, the dosimeter 24 is a separate component from other components of the circuit 22.

The dosimeter 24 is positioned adjacent to the circuit 22 such that the dosimeter 24 is responsive to the same or similar radiation exposure as the circuit 22. For example, the dosimeter 24 is mounted on the same circuit board 20 or within a same integrated circuit. The circuit 22 and the dosimeter 24 are spaced away from the beam volume 16. Alternatively, the dosimeter 24 and/or a portion of the board 20 are positioned within the beam volume 16. The dosimeter 24 is separate from the detector 14 for determining patient dosage. Alternatively, the dosimeter 24 is part of the detector 14. The detector 14 maintains an index or reading associated with dosage throughout a life of the circuit 22. The dosage generated by the radiation source 12 over time may be correlated with the life of the circuit 22.

Radiation exposure may vary from place to place within the circuit 22 or circuit board 20. The dosimeter 24 may be positioned adjacent to hotter spots rather than cooler spots and/or adjacent to weaker rather than stronger components. For example, the dosimeter 24 is positioned adjacent to a relatively stronger component in a hotter spot since the stronger component in the hotter spot may fail before a weaker component in a cooler spot.

While shown as a single dosimeter 24, a plurality of dosimeters in adjacent or dispersed locations may be provided. For example, two or more dosimeters 24 are provided on a same or different circuit boards 20 and/or circuits 22. In one embodiment, three, four, or five dosimeters are provided on the same circuit board, such as providing four dosimeters at corners and a fifth dosimeter in the center of the circuit board 20. An average dosage, highest dosage, individual dosages or combination of dosage readings from the different dosimeters may be used.

The measurement circuit 26 is positioned on the circuit board 20, adjacent to the circuit 22 and the dosimeter 24. Alternatively, the measurement circuit 26 is spaced from the dosimeter 24, the circuit 22 or the circuit board 20. For example, the measurement circuit 26 is a handheld or manufacturer based device for measuring the dosimeter 24 when in the system 10 or after a removal from the system 10.

Figure 3:
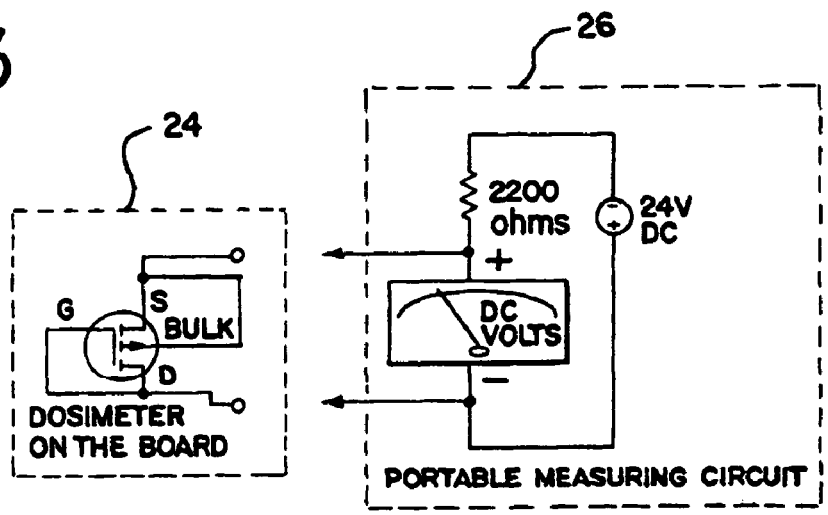
FIG. 3 is a circuit diagram of one embodiment of a circuit for measuring dosage from a dosimeter.

FIG. 3 shows one example of the measurement circuit 26 and a transistor based dosimeter 24. For the dosimeter 24, the gate terminal is tied to the drain terminal, and a bulk semiconductor terminal is tied to the source terminal of the dosimeter 24. Other arrangements may be provided. The measurement circuit 26 is a volt meter or other device for determining a threshold of the transistor used as the dosimeter 24. Threshold voltage is the gate to source voltage at which the transistor is in full induction, and may change linearly or non-linearly with exposure to radiation. In the embodiment shown in FIG. 3, the measurement circuit 26 is a volt meter with a source of approximately 10 milliamps.

As the transistor's threshold voltage increases, the current is less.

The measurement circuit 26 is operable to measure an output characteristic of the dosimeter 24. For example, the threshold voltage initially starts at about −3 volts. Other thresholds may be provided. The initial threshold voltage before exposure to significant dosage is recorded or stored, such as a being stored electronically or printed adjacent to or on the dosimeter 24 or at another location. One example change over a life of a dosimeter 24 and associated circuit board 20 given an exposure of 520,000 MU, the threshold voltage may increase to a magnitude of about −10 volts. Other relative threshold changes may be provided. In yet other alternative embodiments, different characteristics of a dosimeter 24 are used to provide output representation of dosage.

Where the measurement circuit 26 is mounted to or near the circuit board 20, the measurement circuit 26 may communicate with a control processor or other circuits for generation of warning signals or current dosage indication. The system 10 reads the dosimeter 24 periodically, logging the values and/or issuing a warning if the circuit 22 or associated circuit board 20 is approaching the end of the design life due to radiation exposure. Alternatively, the measurement circuit 26 operates independently of the circuit 22 or other circuits to output either a visible indicator or electronic data for a given or series of measurements.

As an alternative or additionally, the measurement circuit 26 is separate from the circuit board 20 or the dosimeter 24. The measurement circuit 26 may be used for measuring the dosimeter 24 while still in the system 10 or while removed from the system 10. A measuring may be made without powering up the entire circuit 22. For example, a tester keeps the measurement circuit 26 on a workbench at the manufacturer for testing the circuit board 20 removed from medical system 10 and shipped to the manufacturer. Exposed contacts are provided on the dosimeter 24 for measuring the output or dosage indication. The dosimeter 26 may be hand held or mounted to a diagnostic system, such as a card reader with a mechanical and electrical mount for the circuit board 20.

While shown as a meter in one representation, the measurement circuit 26 may include a memory and/or display for providing a listing of different readings at different times of the dosimeter 24. For example, a memory is provided in a portion of the measurement circuit mounted on the circuit board 20 adjacent to the dosimeter 24. A hand-held or remote portion of the measurement circuit 26 then connects with the memory for outputting the measure dosage information to a user. In yet other embodiments, the measurement circuit 26 connects through a computer network or phone lines for communicating dosage measurements to remote locations.

Figure 4:
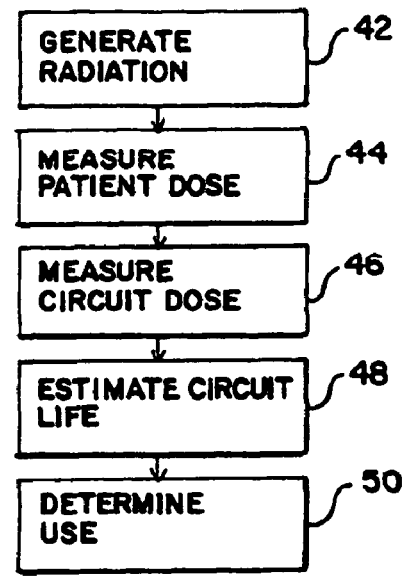
FIG. 4 is a flow chart diagram of one embodiment of a method for estimating circuit life in a radiation environment.

FIG. 4 shows a method of one embodiment for estimating circuit life in a radiation-based medical system. The method is implemented using the system 10 shown in FIGS. 1 and 3 or different systems. The acts may be performed in the order shown or a different order. Additional, different or fewer acts may be provided. For example, act 44, 48 and/or 50 are not provided.

In act 42, radiation is generated with a medical system. For example, a linear accelerator generates x-ray photons or other types of radiation for treatment and/or imaging of a patient. The radiation is directed towards a specific region of the patient. Collimators or other structures are used to shape and guide the radiation beam. The electronics of the imaging system used for generating the radiation are spaced from the possible beam locations, but may alternatively be within a possible or actual beam volume. Items that are not in the actual beam volume 16 may be within the fringes of the beam volume. In one embodiment, the circuit 22 receives radiation at a rate equivalent to about 1.5% of the rate at which the patient receives radiation at isocenter. Thus, in a treatment where the patient receives 100 MU (equivalent to 100 centigrays at isocenter), the circuit receives 1.5 MU.

In act 44, the radiation output relative to a patient is measured with a circuit. A detector is positioned adjacent to the source of radiation, between the source of radiation of the patient or on an opposite side of the patient as the source of radiation. The detector senses an amount of radiation, such as a dosage output by the radiation source throughout a course of treatment during a same session. The total exposure of a patient to radiation during a treatment or imaging session is measured and limited. Alternatively, the dosage applied to the patient is not measured where the radiation source is calibrated or used for lower power applications, such as imaging.

In act 46, radiation exposure of a circuit to radiation is measured. The exposure of the circuit is measured separate from measuring the dosage applied relative to a patient. Alternatively, the dosage applied to the patient is recorded and used as an indication of exposure of the circuit to radiation. Any measurement may be used, such as measuring a voltage of a threshold characteristic of a transistor. Accumulated exposure over a time period, such as associated with treatment of multiple patients using a same imaging system over years, is measured. A single measurement or a series of measurements are provided.

The measurement is performed by circuitry integrated with or adjacent to one or more dosimeters. Alternatively or additionally, the measurements are performed by devices that are attachable but otherwise remote from the dosimeter. The measurement indicates total exposure over time of a circuit, circuit board or other components. The dosimeter is positioned adjacent to the component of interest to more accurately represent the exposure to the component. A component of the circuit used for other purposes may be measured to also act as a dosimeter. Alternatively, the dosimeter is spaced from the component of interest where a relationship between exposure of the dosimeter and the component location is known.

In act 48, a remaining life of a circuit board is estimated as a function of measured radiation exposure. It is difficult to determine which components within a circuit operate within tolerance, such as during a whole board functional test. A radiation damaged board may contain out of specification components, but the whole board test may fail to indicate or identify such components. Like-component testing may provide more detailed information about the behavior of each part, but is more time consuming. By using the dosage determination for a given circuit or component, the life of the component may be estimated as a function of radiation exposure.

The remaining life of a component or circuit is determined from the expected life in the measure radiation exposure. Different levels of accuracy and estimation are provided. The sensitivity of the dosimeter, the accuracy of the expected degradation of a component due to a given amount of radiation exposure, or other factors may alter the accuracy. The exposure limit for any given component of the circuit is determined by measuring one or more parameters of the components. The components are exposed to a known amount of radiation. The previously measured parameters are remeasured. A determination is made as to whether the component is within specifications. The radiation exposures and remeasurements are repeated until a weakest component is identified, a design dosage goal is met, or a failure is detected. Based on the expected exposure of the components in a circuit, the circuit's service life is determined by the life expectancy measured for each of the components of the circuit.

In act 50, the use of a circuit or circuit board is determined as a function of the estimated remaining life. For example, a decision is made whether to scrap or repair a circuit board. A service engineer or technician makes an economic decision based on the estimated remaining life. The estimated remaining life information may be provided in any of various forms, such as a measurement of a total exposure to date, or a specific measurement of remaining life. Where a circuit is determined to have sufficient remaining life for use as a spare part, the board is refurbished. Malfunctioning parts are identified and replaced. Subsequently, generation of radiation, measurement of further accumulated dosage and estimation of remaining life may be performed again for the refurbished circuit after further use and exposure to radiation. An approximate estimation of remaining life of a circuit or circuit board allows for a more refined economic choice between further use of a component or scrapping the component. Other uses of estimated remaining life may be provided, such as maintaining a record of amount of exposure to failure of a circuit board. Records of multiple different circuit boards or circuits may be averaged. The average may be used for standard maintenance. For example, a board is replaced a certain time period short of or at the average life of the board determined by measuring previous failures. The determination of remaining life is made based on an amount of exposure radiation. Failure of an imaging system due to failure of a board may more likely be avoided by proactively replacing the board at a time before or near a likely failure based on the amount of radiation exposure.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for estimating circuit life, the system comprising:
   a medical imaging or treatment system having a circuit;
   a dosimeter adjacent to the circuit such that the dosimeter is responsive to radiation exposure of the circuit, the dosimeter operable to output information for estimating a remaining life of the circuit; and,
   a measurement circuit receiving said output information, wherein said measurement circuit estimates a remaining life of the circuit as a function of said output information;
   wherein the medical imaging system comprises a radiation source with a beam volume directed to a patient area, and wherein the circuit and dosimeter are spaced away from the beam volume and any possible beam volumes.

2. The system of claim 1 wherein the circuit comprises a plurality of electrical components on a circuit board, the dosimeter mounted to the circuit board.

3. The system of claim 1 wherein the radiation source comprises a linear accelerator, and wherein the circuit comprises a dose reading circuit connected with a dose detector within the beam volume, the dose detector separate from the dosimeter.

4. The system of claim 1 wherein the dosimeter comprises a RADFET.

5. The system of claim 1 wherein the dosimeter comprises a commercial off-the-shelf transistor.

6. The system of claim 1 wherein the dosimeter is operable to output the radiation exposure free of destruction.

7. The system of claim 6 wherein the dosimeter and the circuit are on a circuit board;
   further comprising a measuring circuit operable to measure the output, the measuring circuit being separate from the circuit board and the medical imaging or treatment system.

8. The system of claim 6 wherein the dosimeter and the circuit are on a circuit board;
   further comprising a measuring circuit operable to measure the output, the measuring circuit being on the circuit board.

9. The system of claim 1 wherein the dosimeter is operable over a range of radiation exposure corresponding with expected exposure to expected failure of a weakest component of the circuit to the radiation exposure.

10. A method for estimating circuit life in a radiation based medical system, the method comprising:
    generating radiation with the medical system;
    measuring radiation exposure of a circuit to the radiation;
    estimating a remaining life of the circuit as a function of the measured radiation exposure; and
    measuring radiation output relative to a patient with the circuit;
    wherein measuring radiation exposure of a circuit comprises measuring radiation exposure of the circuit separate from the radiation output relative to the patient, the circuit separate from any detector of radiation output relative to the patient.

11. A method for estimating circuit life in a radiation based medical system, the method comprising:
    generating radiation with the medical system;
    measuring radiation exposure of a circuit to the radiation; and
    estimating a remaining life of the circuit as a function of the measured radiation exposure;
    wherein generating radiation comprises generating radiation for treament or imaging of a patient, the circuit being spaced from possible beam regions.

12. The method of claim 10 wherein measuring the radiation exposure comprises measuring a threshold voltage of a transistor.

13. The method of claim 10 wherein measuring the radiation exposure comprises measuring with a device separate from the radiation based medical system, the device including a volt meter.

14. The method of claim 10 wherein measuring the radiation exposure comprises measuring with a device on a circuit board with the circuit.

15. The method of claim 10 further comprising:
    determining a use of the circuit as a function of the estimated remaining life.

16. The method of claim 15 wherein determining the use comprises determining whether to use the circuit as a spare part.

17. The method of claim 10 further comprising repeating generating, measuring and estimating.

18. A system for estimating circuit life due to exposure to medical treatment or imaging radiation, the system comprising:
- a radiation source oriented relative to a patient area;
- a circuit board having a circuit operable with the radiation source;
- a dosimeter connected with the circuit board, the dosimeter operable to output information for estimating a remaining life of the circuit; and,
- a measurement circuit receiving said output information, wherein said measurement circuit estimates a remaining life of the circuit as a function of said output information;
- wherein the radiation source comprises a linear accelerator and has a beam volume directed to the patient area, wherein the circuit comprises a dose reading circuit connected with a dose detector within the beam volume, the dose detector separate from the dosimeter, and wherein the circuit and the dosimeter are spaced away from the beam volume.

19. The system of claim 18 wherein the dosimeter comprises a RADFET, a commercial off-the-shelf transistor or combinations thereof, the dosimeter being operable to indicate radiation exposure free of destruction of the dosimeter.

20. The system of claim 18 wherein the dosimeter is operable over a range of radiation exposure corresponding with expected exposure to expected failure of a weakest component of the circuit to the radiation exposure.

* * * * *